United States Patent [19]
Cho et al.

[11] Patent Number: 5,476,671
[45] Date of Patent: Dec. 19, 1995

[54] SYNTHETIC CERAMIDES AND THEIR USE IN COSMETIC COMPOSTIONS

[75] Inventors: Suk H. Cho, Bogota; Laura J. Frew, Ridgewood; Prem Chandar, Closter, all of N.J.; Stephen A. Madison, New City, N.Y.

[73] Assignee: Chesebrough-Pond's USA Co., Division of Conopco, Inc., Greenwich, Conn.

[21] Appl. No.: 431,344

[22] Filed: Apr. 28, 1995

Related U.S. Application Data

[63] Continuation of Ser. No. 169,828, Dec. 17, 1993, abandoned.

[51] Int. Cl.$^6$ .................. A61K 7/48; C07F 9/02
[52] U.S. Cl. .................. 424/70.1; 424/61; 424/401; 514/23; 514/844; 514/846; 514/937; 514/938; 536/1.11; 536/18.7; 558/170; 564/192; 564/201; 564/203
[58] Field of Search .................. 424/70.1, 61, 401; 514/23, 844, 846, 937, 938; 536/1.11; 558/170; 564/192, 201, 203

[56] References Cited

U.S. PATENT DOCUMENTS

| | | | |
|---|---|---|---|
| 3,644,204 | 2/1972 | Heins et al. | 252/8.8 |
| 4,778,823 | 10/1988 | Kawamata et al. | 514/625 |
| 4,985,547 | 1/1991 | Yano et al. | 536/4.1 |
| 5,028,416 | 7/1991 | Yano et al. | 424/59 |
| 5,071,971 | 12/1991 | Yano et al. | 424/59 |
| 5,175,321 | 12/1992 | Ohashi et al. | 554/63 |
| 5,198,210 | 3/1993 | Critchley et al. | 424/78.05 |
| 5,206,020 | 4/1993 | Critchley et al. | 424/401 |
| 5,208,355 | 5/1993 | Scott | 554/37 |
| 5,338,491 | 8/1994 | Connor et al. | 252/548 |

FOREIGN PATENT DOCUMENTS

| | | |
|---|---|---|
| 0282816 | 9/1988 | European Pat. Off. . |
| 0482860 | 4/1992 | European Pat. Off. . |
| 0534286 | 3/1993 | European Pat. Off. . |
| 1244505 | 9/1971 | United Kingdom . |
| WO93/19145 | 9/1993 | WIPO . |

OTHER PUBLICATIONS

Imokawa, Genji et al. "Water-retaining Function in the Stratum Corneum and its Recovery Properties by Synthetic Pseudoceramides", J. Soc. Cosmet. Chem. 40, (Sep./Oct. 1989), pp. 273–285.
Abstract of JP 63/178842.

*Primary Examiner*—Jyothsna Venkat
*Attorney, Agent, or Firm*—Rimma Mitelman

[57] ABSTRACT

A novel pseudoceramide which has improved dispersibility in aqueous solutions and which can be produced by an economical manufacturing process. The process for producing new pseudoceramides and cosmetic compositions containing the new pseudoceramides are also disclosed.

9 Claims, No Drawings

SYNTHETIC CERAMIDES AND THEIR USE IN COSMETIC COMPOSTIONS

This is a continuation, application of Ser. No. 08/169,828, filed Dec. 17, 1993, now abandoned.

FIELD OF THE INVENTION

The invention relates to new synthetic ceramides, their synthesis, and their use in compositions for topical application to human skin, hair, and nails.

BACKGROUND OF THE INVENTION

Layers of lipids in stratum corneum of the skin form a "water barrier" which prevents water loss from the skin. Known classes of stratum corneum lipids include ceramides, free fatty acids, sterols and sterol esters, and phospholipids, with ceramides being a major component.

Although several species of natural ceramides have been identified, these ceramides must be obtained through a lengthy process involving the extraction of ceramides from natural sources. Thus, the availability of natural ceramides is limited and their cost is very high.

Several analogs of natural ceramides, known as pseudoceramides, have been synthesized. Pseudoceramides look similar but are not identical to ceramides. The water retaining function in stratum corneum of pseudoceramides has been described. See for example, J. Soc. Cosmet. Chem., 40, 273–285 (1989). Cosmetic compositions are known which utilize pseudoceramides to control water loss and/or to repair damaged (e.g., dry, flaky, chapped, wrinkled) skin by replacing the skin's natural lipids. See for example, U.S. Pat. Nos. 5,206,020 (Critchley et al.), 5,198,210 (Critchley et al.), 5,175,321 (Ohashi et al.), 4,985,547 (Yano et al.), and 4,778,823 (Kawamata et al.). European Patent Application 556,957 discloses compositions which are said to be particularly effective for prevention or amelioration of skin wrinkling, chapping or ageing, the compositions including (i) a ceramide or a pseudoceramide; (ii) a fatty acid or a fatty alcohol; and (iii) cholesterol or a plant sterol.

Unfortunately, pseudoceramides are still expensive, albeit not as expensive as natural ceramides. The ternary active system referred to in the European Application 556,957 is even more expensive than a single active pseudoceramide-based compositions, due to a relatively high cost of cholesterol. Thus, there is a continuing need for more cost-effective pseudoceramide-containing compositions, i.e., more efficacious and lower cost pseudoceramides and/or more beneficial reduced cost combinations of pseudoceramides with other ingredients.

Accordingly, it is an object of the present invention to provide novel pseudoceramides while avoiding the disadvantages of prior art.

It is another object of the present invention to provide processes of preparing novel pseudoceramides.

It is yet another object of the invention to provide novel pseudoceramides which can be obtained at a relatively low cost.

It is still another object of the invention to provide compositions containing novel pseudoceramides in combination with other beneficial ingredients which compositions are at least as efficacious as conventional pseudoceramide-containing compositions but which can be produced at a lower cost.

These and other objects of the invention will become more apparent from the detailed description and examples that follow.

SUMMARY OF THE INVENTION

The above objects are attained by the present invention which includes, in part, a novel pseudoceramide (hereinafter termed "neoceramide") of Formula I:

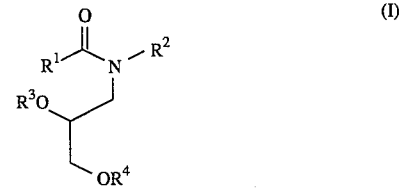

wherein $R^1$ is a linear or branched, saturated or unsaturated, aliphatic hydrocarbon group having from 7 to 48 carbon atoms; $R^1$ may contain a hydroxyl group and/or an aliphatic hydrocarbon ether group.

$R^2$ is a linear or branched, saturated or unsaturated aliphatic hydrocarbon group having from 7 to 48 carbon atoms;

$R^3$ and $R^4$ are the same or different and each is selected from the group consisting of hydrogen, phosphorylethyl amine, phosphorylethyl ammonium, and a sugar moiety. Preferably, in order to ease synthesis, $R^3$ and $R^4$ are not both a group other than hydrogen at the same time.

The combined total number of carbon atoms in $R^1$ and $R^2$ is at least 16, and preferably is at least 18, in order to impart to the neoceramide molecule optimum lipid character.

In the preferred embodiment of the invention $R^1$ is a linear hydrocarbon containing from 7 to 20 carbon atoms, and $R^3$ and $R^4$ are both hydrogens, in order to simplify synthesis of the neoceramides and to attain optimum lipid character and dispersibility of the neoceramides.

Neoceramides disclosed by the present invention are structurally different from the pseudoceramides referred to in the above-identified references in at least the location and distribution of hydroxyl or other polar groups within a molecule. Conventional pseudoceramides contain hydroxyl or other polar groups distributed throughout a molecule at various locations. By contrast, the inventive neoceramides contain two hydroxyl or other polar groups ($R^3$ and $R^4$) in close proximity to each other (i.e., within two carbon atoms) and do not include any polar groups in the $R^2$ chain. Although not wishing to be bound by this theory, it is believed that the particular distribution and proximity of polar groups in the inventive neoceramides imparts surfactant properties to the inventive neoceramides. In any event, the inventive neoceramides and the previously known pseudoceramides behave differently in aqueous liquids, i.e., the inventive neoceramides possess a physical property not shared by pseudoceramides described in the above-identified references. Specifically, the inventive neoceramides form a dispersion in an aqueous liquid in a relatively short period of time whereas the previously known pseudoceramides either do not form dispersions at all or disperse at a substantially slower rate. Thus, the inventive neoceramides may be processed into desired formulations more rapidly and with greater ease than pseudoceramides described in the above-identified references.

A further advantage of the inventive neoceramides is that they may be prepared by processes which are less costly than the traditional pseudoceramide synthesis. Known processes for preparing pseudoceramides are based on the reaction of a glycidyl ether or an epoxyalkane with an ethanolamine, to provide a secondary amine (known as "pseudosphingosine") which is subsequently converted into a pseudoceramide. Unfortunately, glycidyl ether is not commercially available and the steps (typically, two steps) of making the glycidyl ether heretofore had to be included in the pseudoceramide synthesis. Thus, when using glycidyl ether, at least four steps were previously necessary to obtain a pseudoceramide. Although epoxyalkanes are commercially available, using them as staffing materials does not produce neoceramides, but produces pseudoceramides which do not have good dispersibility.

The inventive process, which also forms part of the present invention, does not involve the use of either glycidyl ether or an epoxyalkane or ethanolamine. The process according to the present invention is based on the reaction of a long chain (7 to 48 carbon atoms, preferably 7 to 20 carbon atoms) amine with either glycidol or a halopropanediol, to obtain a novel pseudosphingosine (which is termed hereinafter "neosphingosine"). The alkylamine may be primary or secondary. Preferably, to simplify synthesis, a primary amine is employed.

The present invention also includes compositions for topical application to human skin, hair or nails, which compositions include an effective amount of the inventive neoceramide of Formula I and a cosmetically acceptable vehicle for the neoceramide. The preferred compositions according to the invention include, in addition to the inventive neoceramide, an ingredient selected from the group consisting of a fatty acid, a fatty alcohol, and mixtures thereof. Unexpectedly, it was found as part of the present invention that compositions containing a combination of the inventive neoceramides and an ingredient selected from fatty acids and/or fatty alcohols is as effective, or even more effective, in preventing moisture loss than ternary systems containing previously known pseudoceramides, fatty acids, and cholesterol. Thus, by virtue of using inventive neoceramides instead of previously known pseudoceramides, the need for using an expensive ingredient, i.e., cholesterol, is obviated, without sacrificing the performance of the compositions. Indeed, compositions containing inventive neoceramides in combination with fatty acids/alcohols, perform better than the same compositions which additionally contain cholesterol.

The invention also includes methods of treating skin, hair, or nails by applying topically thereto the inventive neoceramides or the compositions according to the present invention based on inventive neoceramides.

Inventive compositions control water loss or repair damage to the water barrier layer in the stratum corneum. The compositions of the invention are useful in preventing or repairing such skin conditions as dryness, wrinkling, flakiness, chapping, in order to maintain soft, moist, smooth, and supple skin with high elasticity.

DETAILED DESCRIPTION OF THE INVENTION

The Neoceramide

In its first aspect, the invention provides the neoceramides having a general Formula I as hereinbefore defined. $R^1$ is most preferably an aliphatic hydrocarbon group containing from 12 to 20 carbon atoms, which may contain a hydroxyl group and/or an ether group, but more preferably is non-hydroxylated and non-etherified; $R^2$ is preferably a straight chain hydrocarbon group containing from 10 to 20 carbon atoms, in order to simplify synthesis and to attain optimum performance of the neoceramides.

With regard to $R^3$ and $R^4$, phosphorylethyl amine and phosphorylethyl ammonium are represented by Formulae IV and V, respectively:

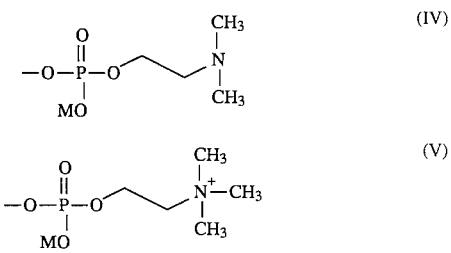

wherein M is hydrogen or an alkali metal.

The term "sugar moiety" as used herein means any saccharide which contains at least one cyclic sugar. Mono-, di-, and oligosaccharides are included within the term "sugar moiety." Suitable sugar moieties include but are not limited to glucopyranoside, fructofuranoside, galactopyranoside, sucrose, and lactobionic esters. The preferred sugar moieties are sucrose and glucopyranoside due to their ready availability and optimum cost.

In the most preferred embodiment of the invention $R^3$ and $R^4$ are both hydrogens in order to lower the cost of the resulting neoceramide and to attain maximum dispersibility of the neoceramides in aqueous solvents.

Specific examples of the neoceramides according to the invention include but are not limited to those having structures 1–10, as follows:

STRUCTURE 1

N-(2,3-dihydroxypropyl)-N-dodecyl Hexadecanamide

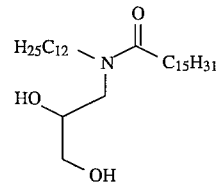

STRUCTURE 2

N-(2, 3-dihydroxypropyl)-N-dodecyl-2-hydroxyoctanamide

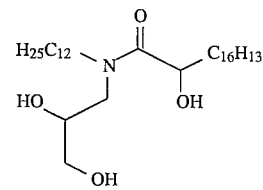

STRUCTURE 3

N-(2,3-dihydroxypropyl)-N-dodecyl-2-hydroxyhexadecanamide

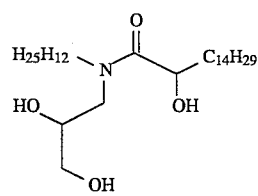

STRUCTURE 4

N-(2,3-dihydroxypropyl)-N-hexadecyl Hexadecanamide

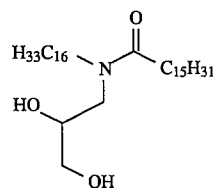

STRUCTURE 5

N-(2,3-dihydroxypropyl)-N-hexadecyl-2-hydroxyoctanamide

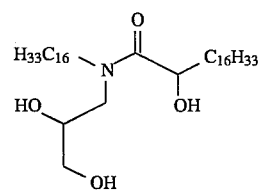

STRUCTURE 6

N-(2,3-dihydroxypropyl)-N-hexadecyl-2-hydroxyhexadecanamide

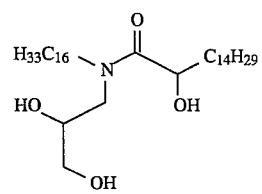

STRUCTURE 7

N-(2, 3-dihydroxypropyl)-N-tetradecyl-2-hydroxyoctanamide

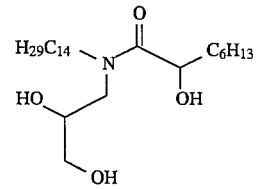

STRUCTURE 8

N-(2,3-dihydroxypropyl)-N-tetradecyl Hexadecanamide

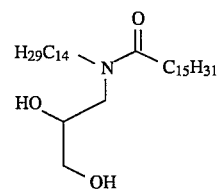

STRUCTURE 9

N-(2,3-dihydroxypropyl)-N-tetradecyl-2-hydroxyhexadecanamide

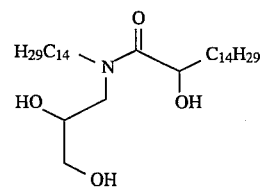

STRUCTURE 10

N-(2,3-dihydroxypropyl)-N-octadecyl Hexadecanamide

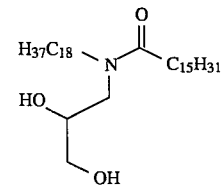

Additional examples of inventive neoceramides include but are not limited to:
N-(2,3-dihydroxypropyl)-N-1-methylhexadecyl-1-methylhexadecanamide
N-(2,3-dihydroxypropyl)-N-1-methyldecyl-1-ethyltetradecanamide
N-(2,3-dihydroxypropyl)-N-1-ethyldodecyl-1-octyloctadecanamide N-(2,3-dihydroxypropyl)-N-1-butyltetradecyl-2-methyl-hexadecanamide
N-(2,3-dihydroxypropyl)-N-2-butyloctyl-2-ethyloctadecanamide
N-(2,3-dihydroxypropyl)-N-2-metylhexadecyl-2-butyleicosanamide
N-(2,3-dihydroxypropyl)-N-2-ethyldodecyl-2-propyldecanamide
N-(2,3-dihydroxypropyl)-N-2-pentyloctadecyl-2-pentyldecanamide
N-(2,3-dihydroxypropyl)-N-3-methylhexadecyl-2-methyldodecanamide
N-(2,3-dihydroxypropyl)-N-3-ethyltetradecyl-2-propyloctadecanamide
N-(2,3-dihydroxypropyl)-N-3-octylhexadecyl-2-ethylhexadecanamide
N-(2,3-dihydroxypropyl)-N-3-propyldocosyl-3-methyldodecanamide
N-(2,3-dihydroxypropyl)-N-4-propyldecyl-3-ethyloctadecanamide
N-(2,3-dihydroxypropyl)-N-4-ethylhexadecyl-3-hexyldodecanamide
N-(2,3-dihydroxypropyl)-N-4-hexylhexadecyl-4-methylhexadecanamide
N-(2,3-dihydroxypropyl)-N-6-propyltetradecyl-4-butylhexadecanamide
N-(2,3-dihydroxypropyl)-N-decyl-4-methylhexadecanamide
N-(2,3-dihydroxypropyl)-N-dodecyl-4-methylhexadecanamide
N-(2,3-dihydroxypropyl)-N-tetradecyl-4-methylhexadecanamide
N-(2,3-dihydroxypropyl)-N-hexadecyl-4-methyldecanamide
N-(2,3-dihydroxypropyl)-N-hexadecyl-4-methyldodecanamide
N-(2,3-dihydroxypropyl)-N-hexadecyl-4-methyltetraadecanamide
N-(2,3-dihydroxypropyl)-N-hexadecyl-4-methyloctadecanamide
N-(2,3-dihydroxypropyl)-N-eicosyl-4-methylhexadecanamide
N-(2,3-dihydroxypropyl)-N-docosyl-4-methylhexadecanamide
N-(2,3-dihydroxypropyl)-N-hexadecyl-4-methyleicosanamide
N-(2,3-dihydroxypropyl)-N-hexadecyl-3-ethylhexadecanamide
N-(2,3-dihydroxypropyl)-N-hexadecyl-3-ethyleicosanamide
N-(2,3-dihydroxypropyl)-N-eicosyl-3-ethylhexadecanamide
N-(2,3-dihydroxypropyl)-N-dodecyl-3-ethylhexadecanamide
N-(2,3-dihydroxypropyl)-N-tetradecyl-3-ethylhexadecanamide
N-(2,3-dihydroxypropyl)-N-octadecyl-3-ethylhexadecanamide
N-(2,3-dihydroxypropyl)-N-docosyl-3-ethylhexadecanamide
N-(2,3-dihydroxypropyl)-N-hexadecyl-3-ethyltetradecanamide
N-(2,3-dihydroxypropyl)-N-hexadecyl-3-ethyldodecanamide
N-(2,3-dihydroxypropyl)-N-hexadecyl-3-ethyloctadecanamide
N-(2,3-dihydroxypropyl)-N-hexadecyl-3-ethyldecanamide
N-(2,3-dihydroxypropyl)-N-hexadecyl-3-ethyloctanamide
N-(2,3-dihydroxypropyl)-N-3-hexadecenyl-3-ethyloctanamide
N-(2,3-dihydroxypropyl)-N-4-decenyl-3-ethyloctanamide
N-(2,3-dihydroxypropyl)-N-3-tetradecenyl-3-ethyloctanamide
N-(2,3-dihydroxypropyl)-N-6-dodecenyl-3-ethyldecanamide
N-(2,3-dihydroxypropyl)-N-8-eicosenyl-3-ethyloctanamide
N-(2,3-dihydroxypropyl)-N-2-(4-methyl)hexadecenyl-3-ethyloctanamide
N-(2,3-dihydroxypropyl)-N-hexadecyl-3-octeneamide
N-(2,3-dihydroxypropyl)-N-1-methylhexadecyl-4-deceneamide
N-(2,3-dihydroxypropyl)-N-2-ethyltetradecyl-3-octeneamide
N-(2,3-dihydroxypropyl)-N-5-butyloctadecyl-2-eicosencamide
N-(2,3-dihydroxypropyl)-N-2-propyldodecyl-2-tetradeceneamide
N-(2,3-dihydroxypropyl)-N-hexadecyl-3-dodeceneamide
N-(2,3-dihydroxypropyl)-N-hexadecyl-4-heptadeceneamide
N-(2,3-dihydroxypropyl)-N-3-methylpentadecyl-2-docosceneamide
N-(2-hydroxy-3-glucopyranosyl propyl)-N-hexadecyl hexadecanamide
N-(2-hydroxy-3-glucopyranosyl propyl)-N-hexadecyl decanamide
N-(2-hydroxy-3-glucopyranosyl propyl)-N-hexadecyl docosanamide
N-(2-hydroxy-3-glucopyranosyl propyl)-N-octadecyl octadecanamide
N-(2-hydroxy-3-glucopyranosyl propyl)-N-hexadecyl-2-hydroxydecanamide
N-(2-hydroxy-3-glucopyranosyl propyl)-N-hexadecyl-2-hydroxyhexadecanamide
N-(2-hydroxy-3-glucopyranosyl propyl)-N-hexadecyl-2-hydroxytetradecanamide
N-(2-hydroxy-3-glucopyranosyl propyl)-N-hexadecyl-2-hydroxydodecanamide
N-(2-hydroxy-3-glucopyranosyl propyl)-N-hexadecyl-2-hydroxyoctanamide
N-(2-hydroxy-3-glucopyranosyl propyl)-N-decyl-2-hydroxyhexadecanamide
N-(2-hydroxy-3-glucopyranosyl propyl)-N-dodecyl-2-hydroxyhexadecanamide
N-(2-hydroxy-3-glucopyranosyl propyl)-N-eicosyl-2-hydroxydecanamide
N-(2-hydroxy-3-glucopyranosyl propyl)-N-hexadecyl decanamide
N-(2-hydroxy-3-glucopyranosyl propyl)-N-hexadecyl hexadecanamide
N-(2-hydroxy-3-glucopyranosyl propyl)-N-hexadecyl-1-methylhexadecanamide
N-(2-hydroxy-3-glucopyranosyl propyl)-N-octadecyl-1-ethylhexadecanamide
N-(2-hydroxy-3-fructofuranosyl propyl)-N-decyl-1-propylhexadecanamide
N-(2-hydroxy-3-fructofuranosyl propyl)-N-dodecyl-1-butyltetradecanamide
N-(2-hydroxy-3-lactobianyl propyl)-N-eicosyl-1-octylhexadecanamide
N-(2-hydroxy-3-lactobianyl propyl)-N-docosyl-1-methylhexadecanamide
N-(2-hydroxy-3-lactobianyl propyl)-N-hexadecyl-2-methylhexadecanamide N-(2-hydroxy-3-glucopyranosyl propyl)-N-2-hexadecenyl hexadecanamide
N-(2-hydroxy-3-glucopyranosyl propyl)-N-4-tetradecenyl-3-propylhexadecanamide
N-(2-hydroxy-3-glucopyranosyl propyl)-N-4-octadecenyl-2-ethylhexadecanamide
N-(2-hydroxy-3-glucopyranosyl propyl)-N-6-dodecenyl-2-butyl-hexadecanamide
N-(2-hydroxy-3-glucopyranosyl propyl)-N-4-decenyl-4-hexylhexadecanamide
N-(2-hydroxy-3-glucopyranosyl propyl)-N-6-hexadecenyl-2-butylhexadecanamide
N-(2-hydroxy-3-fructofuranosyl propyl)-N-2-dodecenyl-1-methyltetradecanamide
N-(2-hydroxy-3-fructofuranosyl propyl)-N-4-tetradecenyl-1-ethyloctadecanamide
N-(2-hydroxy-3-fructofuranosyl propyl)-N-6-eicosenyl-1-propyltetradecanamide
N-(2-hydroxy-3-fructofuranosyl propyl)-N-6-octadecenyl-1-hexyleicosanamide
N-(2-hydroxy-3-fructofuranosyl propyl)-N-2-dodecenyl-1-butyltetradecanamide
N-(2-hydroxy-3-fructofuranosyl propyl)-N-2-hydroxydodecyl-3-(1-butyl)tetradeceneamide
N-(2-hydroxy-3-lactobianyl propyl)-N-2-eicosenyl-1-octylhexadecanamide
N-(2-hydroxy-3-lactobianyl propyl)-N-4-docosenyl-1-propyltetradecanamide
N-(2-hydroxy-3-lactobianyl propyl)-N-5-dodecenyl-2-butyloctadecanamide
N-(2-hydroxy-3-lactobianyl propyl)-N-2-octenyl-2-pentylhexadecanamide
N-(2-hydroxy-3-lactobianyl propyl)-N-3-methyleicosyl-1-octylhexadecanamide
N-(2-hydroxy-3-lactobianyl propyl)-N-2-butyleicosyl-1-octylhexadecanamide
N-(2-hydroxy-3-lactobianyl propyl)-N-1-methylhexadecyl-1-methylhexadecanamide
N-(2-hydroxy-3-glucopyranosyl propyl)-N-1-methyltetradecyl-2-methylhexadecanamide
N-(2-hydroxy-3-glucopyranosyl propyl)-N-1-methyldecyl-1-methylhexadecanamide
N-(2-hydroxy-3-fructofuranosyl propyl)-N-1-butylhexadecyl-2-ethyltetradecanamide
N-(2-hydroxy-3-glucopyranosyl propyl)-N-1-octyldodecyl-3-methylhexadecanamide
[N-(2-(O-(2-trimethylammonium ethyl)phosphoryl)-3-hydroxy propyl)-N-hexadecyl-1-methylhexadecanamide] chloride
[N-(3-(O-(2-trimethylammonium ethyl)phosphoryl)-2-hydroxy propyl)-N-3-methyl-hexadecyl-4-ethylhexadecanamide] bromide
[N-(2-(O-(2-trimethylammonium ethyl)phosphoryl)-3-hydroxy propyl)-N-1-hexyl-tetradecyl-2-butyldodecanamide] chloride
[N-(3-(O-(2-trimethylammonium ethyl)phosphoryl)-2-hydroxy propyl)-N-1-methylhexadecyl-4-hexyldecanamide] sulfate
[N-(2-(O-(2-trimethylammonium ethyl)phosphoryl)-3-hydroxy propyl)-N-2-decyl-dodecyl-6-butyleicosanamide] sulfate
[N-(2-(O-(2-trimethylammonium ethyl)phosphoryl)-3-hydroxy propyl)-N-2-hexadecenyl-1-methylhexadecanamide] chloride
[N-(3-(O-(2-trimethylammonium ethyl)phosphoryl)-2-hydroxy propyl)-N-3-tetradecenyl-1-methylhexadecanamide] sulfate
[N-(2-(O-(2-trimethylammonium ethyl)phosphoryl)-3-hydroxy propyl)-N-3-butylhexadecyl-1-methyltetradecanamide] bromide
[N-(2-(O-(2-trimethylammonium ethyl)phosphoryl)-3-hydroxy propyl)-N-2-dodecenyl-1-methyldodecanamide] chloride
[N-(2-(O-(2-trimethylammonium ethyl)phosphoryl)-3-glucopyranosyl propyl)-N-2-eicosenyl-1-methylhexadecanamide] bromide
[N-(2-(O-(2-trimethylammonium ethyl)phosphoryl)-3-glucopyranosyl propyl)-N-decenyl-1-propyloctanamide] sulfate
[N-(2-(O-(2-trimethylammonium ethyl)phosphoryl)-3-hydroxy propyl)-N-3-butylhexcadecyl-1-methylhexadecanamide] chloride
[N-(3-(O-(2-trimethylammonium ethyl)phosphoryl)-2-glucopyranosyl propyl)-N-4-butyldodecyl-1-methylhexadecanamide] sulfate
[N-(2-(O-(2-trimethylammonium ethyl)phosphoryl)-3-hydroxy propyl)-N-4-decenyl-2-propylhexadecanamide] bromide
[N-(2-(O-(2-trimethylammonium ethyl)phosphoryl)-3-glucopyranosyl propyl)-N-4-propylhexadecyl-2-hexyldodecanamide] chloride
[N-(3-(O-(2-trimethylammonium ethyl)phosphoryl)-2-hydroxy propyl)-N-3-hexadecenyl-3-butyldecanamide] sulfate
[N-(2-(O-(2-trimethylammonium ethyl)phosphoryl)-3-hydroxy propyl)-N-hexadecyl-1-methylhexadecanamide] chloride
[N-(2-(O-(2-trimethylammonium ethyl)phosphoryl)-3-glucofuranosyl propyl)-N-hexadecyl-1-methyldecanamide] chloride
[N-(2-(O-(2-trimethylammonium ethyl)phosphoryl)-3-hydroxy propyl)-N-3-butylhexadecyl-1-methylhexadecanamide] sulfate
[N-(3-(O-(2-trimethylammonium ethyl)phosphoryl)-2-hydroxy propyl)-N-2 hexadecenyl-1-methylhexadecanamide] chloride
[N-(2-(O-(2-trimethylammonium ethyl)phosphoryl)-3-glucofuranosyl propyl)-N-3-methylhexadecyl-2-butyldodecanamide] bromide
[N-(2-(O-(2-trimethylammonium ethyl)phosphoryl)-3-hydroxy propyl)-N-3-methylheptadecyl-3-propylpentadecanamide] sulfate
[N-(2-(O-(2-trimethylammoniumethyl)phosphoryl)-3-glucofuranosyl propyl)-N-hexcadecyl-1-hexadeceneamide] chloride
[N-(2-(O-(2-trimethylammonium ethyl)phosphoryl)-3-hydroxy propyl)-N-3-propyldecyl-1-propyltetradecanamide] sulfate
N-(2-(O-(2-dimethylamino ethyl)phosphoryl)-3-hydroxy propyl)-N-2-decyldodecyl-6-butyleicosanamide
N-(2-(O-(2-dimethylamino ethyl)phosphoryl)-3-glucopyranosyl propyl)-N-2-butyldodecyl-2-octyldodecanamide
N-(2-(O-(2-dimethylamino ethyl)phosphoryl)-3-fructofuranosyl propyl)-N-2-ethyltetradecyl-1-propyloctadecanamide
N-(2-(O-(2-dimethylamino ethyl)phosphoryl)-3-hydroxy propyl)-N-2-propyloctadecyl-1-hexylhexadecanamide
N-(2-(O-(2-dimethylamino ethyl)phosphoryl)-3-hydroxy propyl)-N-3-pentyleicosyl-2-propyltetradecanamide
N-(2-(O-(2-dimethylamino ethyl)phosphoryl)-3-hydroxy propyl)-N-3-hexyldodecyl-2-methyldecanamide
N-(2-(O-(2-dimethylamino ethyl)phosphoryl)-3-hydroxy propyl)-N-2-hexyldecyl-6-octyldecanamide
N-(3-(O-(2-dimethylamino ethyl)phosphoryl)-2-hydroxy propyl)-N-2-decenyl-6-butyldecanamide N-(2-(O-(2-dimethylamino ethyl)phosphoryl)-3-hydroxy propyl)-N-2-dodecenyl-2-octyldecanamide
N-(3-(O-(2-dimethylamino ethyl)phosphoryl)-3-hydroxy propyl)-N-2-tetradecenyl-2-ethyldodecanamide
N-(3-(O-(2-dimethylamino ethyl)phosphoryl)-2-hydroxy propyl)-N-2-hexadecenyl-2-propyltetradecanamide
N-(3-(O-(2-dimethylamino ethyl)phosphoryl)-2-hydroxy propyl)-N-3-dodecenyl-2-methyloctadecanamide
N-(2-(O-(2-dimethylamino ethyl)phosphoryl)-3-hydroxy propyl)-N-4-hexadecenyl-3-propyltetradecanamide
N-(3-(O-(2-dimethylamino ethyl)phosphoryl)-2-hydroxy propyl)-N-4-tetradecenyl-2-butyldecanamide
N-(3-(O-(2-dimethylamino ethyl)phosphoryl)-2-hydroxy propyl)-N-3-pentadecenyl-2-hexylhexadecanamide
N-(3-(O-(2-dimethylamino ethyl)phosphoryl)-2-hydroxy propyl)-N-decyl-6-octyldecanamide
N-(3-(O-(2-dimethylamino ethyl)phosphoryl)-2-hydroxy propyl)-N-dodecyl-1-methyltetradecanamide
N-(3-(O-(2-dimethylamino ethyl)phosphoryl)-2-hydroxy propyl)-N-1-ethylhexadecyl octyldecanamide
N-(3-(O-(2-dimethylamino ethyl)phosphoryl)-2-hydroxy propyl)-N-2-hexyldecyl-6-octyldecanamide
N-(2-(O-(2-dimethylamino ethyl)phosphoryl)-3-hydroxy propyl)-N-1-methylhexadecyl-2-propyldodecanamide
N-(2-(O-(2-dimethylamino ethyl)phosphoryl)-3-hydroxy propyl)-N-2-butyloctadecyl octadecanamide
N-(2-(O-(2-dimethylamino ethyl)phosphoryl)-3-hydroxy propyl)-N-3-propyltetradecyl decanamide
N-(3-(O-(2-dimethylamino ethyl)phosphoryl)-3-hydroxy propyl)-N-3-methyldodecyl-2-octyltetradecanamide
N-(2-(O-(2-dimethylamino ethyl)phosphoryl)-3-hydroxy propyl)-N-3-butylhexadecyl-3-hexylhexadecanamide
N-(2-(O-(2-dimethylamino ethyl)phosphoryl)- 3-hydroxy-propyl)-N-2-hexyldecyl-6-octyldecanamide
N-(3-(O-(2-dimethylamino ethyl)phosphoryl)-2-hydroxy-propyl)-N-1-methyltetradecyl-2-methyltetradecanamide
N-(3-(O-(2-dimethylamino ethyl)phosphoryl)-2-hydroxy-propyl)-N-1-propyloctadecyl-2-ethyloctadecanamide

Synthesis of the Neoceramides

The inventive neoceramides are preferably synthesized via a process according to the present invention. The inventive process utilizes readily available starting ingredients. The inventive process employing halopropanediol is preferred due to its lowest cost compared to the other inventive process, i.e. the process employing glycidol.

The process according to the present invention is based on the reaction of an alkylamine with glycidol or a halopropanediol to obtain a secondary amine ("neosphingosine") of Formula II:

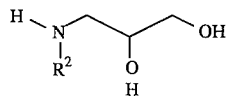

In the preferred embodiment of the invention, the alkylamine is reacted with halopropanediol in order to reduce the cost of synthesis. The alklyamine is preferably a primary amine and it contains from 7 to 48, preferably from 7 to 20, most preferably from 12 to 20, carbon atoms. When glycidol is employed, 0.8–2.0 equivalents, preferably 1.0 equivalent, of glycidol is preferably added, slowly, with stirring, to the premix of one equivalent of the alkylamine in a solvent, in order to minimize the formation of diadduct. Suitable solvents include but are not limited to ethanol, methanol, isopropanol, water; the reaction may also be conducted neat (i.e., in the absence of a solvent). The resulting mixture is preferably heated, preferably under nitrogen blanket, for a sufficient time, e.g. 1–24 hours, typically for a time span of from 3 to 8 hours. The particular time depends on the reaction temperature employed. The heating is conducted at a temperature in the range of from 25° C. to 100° C., preferably from 60° C. to 85° C. Subsequently, the heating is stopped, and the reaction mixture is stirred for a sufficient time to allow the neosphingosine to crystallize out. Generally, the stirring of the reaction mixture overnight allows for sufficient crystallization of neosphingosine.

When halopropanediol is employed, suitable halopropanediols include but are not limited to bromopropanediol, chloropropanediol, and iodopropanediol. Preferably, chloropropanediol is employed due to commercial availability, ease of use and its reduced lachrymal property. When chloropropanediol is employed, one equivalent of chloropropanediol is preferably added, slowly, with stirring to the premix of one equivalent of the alkylamine and 1–3 equivalents, preferably 1–2 equivalents, of potassium carbonate (or sodium carbonate, sodium hydroxide, other inorganic or organic base, etc.,) in a solvent. The same solvents may be employed, as described above for the reaction with glycidol, or the reaction may be conducted neat. The resulting mixture is reacted, preferably with heating, for a sufficient time to form neosphingosine, typically for a time span of 1 to 24 hours, preferably for a time span of from 3 to 8 hrs. The heating is conducted at a temperature in the range from 25° C. to 100° C., preferably from 60° C. to 85° C. Subsequently, the heating is stopped, the salts are filtered, and the neosphingosine of Formula II is obtained after removal of the solvent (if the solvent was employed).

Another process which may be employed to synthesize inventive neoceramides is based on the reaction of aminopropanediol with an alkyl halide, to obtain the neosphingosine of Formula II. When alkyl halide with aminopropanediol is employed, suitable alkyl halides include but are not limited to linear or branched, alkyl chloride, alkyl bromide, alkyl iodide, alkyl methyl chloride, and mixtures thereof. Preferably, linear alkyl chloride is employed due to commercial availability and ease of use. One equivalent of alkyl chloride, one equivalent of aminopropanediol and 1–4 equivalents, preferably 1.5–2.5 equivalents, of potassium carbonate (sodium bicarbonate, sodium carbonate, other inorganic or organic base) in a solvent (or the reaction can be conducted neat) are reacted for a sufficient time to form the neosphingosine of Formula II, typically for a time span of 1 to 24 hours, preferably for a time span of from 3 to 8 hrs. The heating is conducted at a temperature in the range from 25° C. to 100° C., preferably from 60° C. to 85° C. Subsequently, the heating is stopped, the salts are filtered, and neosphingosine of Formula II is obtained, after removal of the solvent (if the solvent was employed).

The inventive process employing halopropanediol is the preferred process according to the present invention.

The resulting neosphingosine of Formula II may be converted into a neoceramide by reacting the neosphingosine with an acid chloride, fatty acid (with or without a catalyst) or a fatty acid ester. In a preferred embodiment of the present invention a fatty acid ester is employed, because use of a fatty acid ester results in a cleaner reaction than acylation of neosphingosine with an acid chloride. Use of fatty acid ester minimizes O-acylation, resulting in a less corrosive process. The resulting neoceramide has the structure depicted in Formula III, which represents the neoceramide of Formula 1 in which both $R^3$ and $R^4$ are hydrogens.

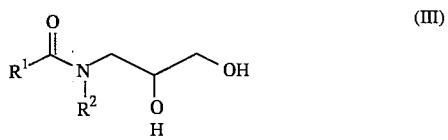

(III)

The neoceramide of Formula III may subsequently be reacted with an ingredient selected from the group consisting of a sugar, a sugar lactone, and mixtures thereof, in the presence of an acid catalyst or an enzyme, to obtain the neoceramide of Formula I wherein $R^3$ and/or $R^4$ is a sugar. This reaction, which is also known as glycosylation reaction, is described in greater detail in U.S. Pat. No. 5,071,971 (Yano et al.), in columns 10–14, which are incorporated by reference herein.

Alternatively, the neoceramide of Formula III may subsequently be reacted with ethylene chlorophosphate to obtain ethylene phosphorylated neoceramide, which subsequently may be reacted with dimethylamine or trimethylamine to obtain the neoceramide of Formula I wherein $R^3$ and/or $R^4$ is phosphorylated. The phosphorylation reaction is described in greater detail in U.S. Pat. No. 5,071,971 (Yano et al.), in columns 9–10, which are incorporated by reference herein.

Compositions for Topical Application

Compositions according to the invention include a) an effective amount of the neoceramide of Formula I; and b) a cosmetically acceptable vehicle for the neoceramide.

The neoceramide of Formula I acts as an active ingredient and the vehicle enables the neoceramide to be dispersed onto the skin and distributed thereon. According to the preferred embodiment of the invention the neoceramide is included in the inventive composition in conjunction with an ingredient selected from the group consisting of fatty acid and/or fatty alcohol, in particular those fatty acids or alcohols with $C_{12}$–$C_{20}$, most preferably $C_{16}$–$C_{18}$, straight or branched alkyl chains. A particularly preferred fatty acid is linoleic acid, since linoleic acid assists in absorption of ultraviolet light and furthermore is a vital component of the natural skin lipids constituting the moisture barrier in the stratum corneum. The weight ratio of the neoceramide to the fatty acid/alcohol is in the range of from 10:1 to 1:10, preferably in the range of from 1:1 to 3:1, and most preferably is 3:1, in order to attain maximum performance at optimum cost.

In the most preferred embodiment of the invention, the inventive compositions are essentially free of cholesterol or plant sterol such as stigmasterol or sitosterol. The term "essentially free of cholesterol" as used herein means that the inventive compositions preferably contain less than 10 wt. % cholesterol by weight of the neoceramide, preferably less than 5 wt. % and optimally less than 1 wt. %. The particular benefit of the inventive compositions is based in part on the discovery that the active system containing the inventive neoceramides and fatty acids or alcohols performs as well as or even better than, the active system based on previously known pseudoceramides in mixtures with fatty acids or alcohols and cholesterol. However, even if the inventive compositions contain cholesterol they still perform better than compositions containing pseudoceramides in combination with fatty acids or alcohols and cholesterol. The amount of cholesterol in the inventive compositions (in the event that such compositions are not essentially free of cholesterol) is such as to obtain the weight ratio of neoceramide:cholesterol in the range of from 3:1 to 1:4, preferably from 1:2 to 2:1, most preferably 1:2 to attain the best performance. However, the most preferred inventive compositions are essentially free of cholesterol in order to optimize both the cost and the performance of compositions.

The Neoceramide

The composition according to the invention includes an effective amount of at least one neoceramide of Formula I as herein defined. Preferred examples of the neoceramides of Formula I are those having Structures 1–10 as defined above.

The amount of the neoceramide, or a mixture thereof, present in the composition according to the invention is from 0.00001 to 50%, preferably from 0.001 to 20% and most preferably from 0.1 to 10% by weight.

The Cosmetically Acceptable Vehicle

The composition according to the invention also comprises a cosmetically acceptable vehicle to act as a dilutant, dispersant or carrier for the neoceramide in the composition, so as to facilitate its distribution when the composition is applied to the skin and/or hair.

Vehicles other than water can include liquid or solid emollients, solvents, humectants, thickeners and powders. Examples of each of these types of vehicles, which can be used singly or as mixture of one or more vehicles, are as follows:

emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcoholeicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow lard, olive oil, palm kernel oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

propellants, such as trichlorofluoromethane, dichlorodifluoromethane, dichlorotetrafluoroethane, monochlorodifluoromethane, trichlorotrifluoro ethane, propane, butane, isobutane, dimethyl ether, carbon dioxide, nitrous oxide;

solvents, such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

powders, such as chalk, talc, fuller's earth, kaolin, starch, gums, colloidal silica, sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the composition, and can, in the absence of other cosmetic adjuncts, form the balance of the composition.

Optional Skin Benefit Materials and Cosmetic Adjuncts

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Oil or Oily Material

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes of forming an emulsion, will normally form up to 90%, preferably from 10 to 80% by weight of the composition.

Emulsifier

The composition according to the invention can also optionally comprise one or more emulsifiers the choice of which will normally determine whether a water-in-oil or oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should generally have an average HLB value of >6.

Examples of suitable emulsifiers include but are not limited to emulsifiers set forth in Table 1 in columns 11–12 of U.S. Pat. No. 5,198,210 (to Critchley et al.), which Table is incorporated by reference herein. It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Water

The composition of the invention can also comprise water, usually up to 98%, preferably from 5 to 80% by weight of the composition.

Silicone Surfactant

The composition of the invention can also optionally comprise a high molecular weight silicone surfactant which can also act as an emulsifier, in place of or in addition to the optional emulsifier(s) already mentioned.

The silicone surfactant is a high molecular weight polymer of dimethyl polysiloxane with polyoxyethylene and/or polyoxypropylene side chains having a molecular weight of from 10,000 to 50,000 and having the structure:

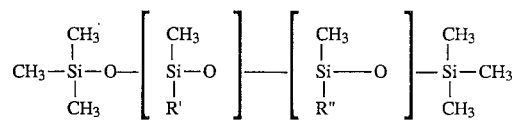

where the groups R' and R" are each chosen from —H, $C_{1-8}$ alkyl and

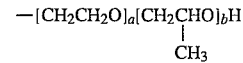

a has a value of from 9 to 115, b has a value of from 0 to 50, x has a value of from 133 to 673, y has a value of from 25 to 0.25.

Preferably, the dimethyl polysiloxane polymer is one in which:

a has a value of from 10 to 114, b has a value of from 0 to 49, x has a value of from 388 to 402, y has a value of from 15 to 0.75.

one of groups R' and R" being lauryl, and the other having a molecular weight of from 1000 to 5000.

A particularly preferred dimethyl polysiloxane polymer is one in which:

a has the value 14 b has the value 13 x has the value 249 y has the value 1.25

The dimethyl polysiloxane polymer is conveniently provided as a dispersion in a volatile siloxane, the dispersion comprising, for example, from 1 to 20% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Other Cosmetic Adjuncts

Examples of conventional adjuncts which can optionally be employed include preservatives, such as parahydroxy benzoate esters; antioxidants, such as butyl hydroxy toluene and vitamin E; humectants, such as glycerol, sorbitol, 2-pyrrolidone-5-carboxylate, dibutylphthalate, gelatin, polyethylene glycol, preferably PEG 200–600; buffers, such as lactic acid together with a base such as triethanolamine or sodium hydroxide; surfactants, such as glycerol ethers and other ceramides of synthetic, animal or plant origin; phospholipids; waxes, such as beeswax, ozokerite wax, paraffin wax; plant extracts, such as Aloe vera, cornflower, witch hazel, elderflower, cucumber; thickeners; activity enhancers; colorants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

Cosmetic adjuncts can form the balance of the composition.

Use of the Composition

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin. The composition can also be applied to hair and nails.

The neoceramides according to the invention have surfactant properties and can therefore also be used, in the form of a composition as herein defined, for cleansing the surface of the human body. In particular, the composition can be used to cleanse the skin to remove makeup or can be employed in a shampoo for cleansing the hair.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin, hair, or nail treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation: When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the present invention but the invention is not limited thereto.

EXAMPLE 1

Specific Examples of Neoceramide Synthesis

Melting points were taken on a Mel-temp in degrees centigrade and are uncorrected. Proton magnetic resonance ($^1$H NMR) spectra were recorded on a Bruker 200 MHz FT spectrometer, Varian 300 MHz FT NMR, or Varian T-60 spectrometer. Carbon magnetic resonance spectra ($^{13}$C NMR) were recorded on a Bruker 200 FT (50 MHz) spectrometer or Varian 300 MHz FT NMR. Proton and carbon chemical shifts are reported in parts per million downfield from tetramethylsilane or other silylated standard (e.g., trimethylsilylpropionate sodium salt) as an internal standard. Spin multiplicities are indicated as follows: s (singlet), d (doublet), t (triplet), q (quartet), m (multiplet), or br (broad). The deuterated NMR solvents contained 99.0–99.8% deuterium in the indicated position and were purchased from the Cambridge Isotopes Laboratories. Infrared spectra (IR) were recorded on a Perkin-Elmer model 298 spectrometer and a Digilab FS 60A FTIR spectrometer using a NaCl cell or KBr solid. Peak intensities are listed as vs (very strong), s (strong), m (medium), w (weak), or br (broad) and peak positions are represented in $cm^{-1}$.

Mass spectroscopy was obtained on a Finnigan Mat SSQ710 GC/MS or on a Lee Scientific Series 600 SFC/GC connected to a Finnigan Mat TSQ70B tandem instrument.

Reagent grade hexane and acetonitrile were used as received. Potassium hydroxide and methyl palmitate obtained from Aldrich Chemical Co. were used as received. Hydroxyoctanoic acid and 2-hydroxyhexadecanoic acid (both were a D,L form) purchased from Lancaster Synthesis were used as received. Methyl 2-hydroxyoctanoate and methyl 2-hydroxyhexadecanoate were prepared using standard esterification procedure.

Synthesis of N-(2,3-dihydroxypropyl)-N-dodecylamine

Dodecylamine (25.02 g, 0.13 mole) was heated to 85° C. Glycidol (10 g, 0.13 mole) was added dropwise. The reaction solution was heated under nitrogen for 3 hours and was stirred overnight at room temperature. A white solid was obtained (crude yield=33.27 g). The solid was recrystalized from hot hexane (crystallized 10.86 g).

m.p.: 74°–77° C.

IR (nujol film, $cm^{-1}$): 3340 st, 3280 m, 3000–2860 br, 1460 st, 1385

$^1$H NMR (200MHz, warm CDCl$_3$ with TMS): δ 0.85 (br t, 3H), 1.3 (br s, 8H), 1.5 (br m, 2H), 2.6 (m, 4H), 3.1 (br s, 3H), 3.7 (m, 3H)

$^{13}$C NMR (50 MHz, warm CDCl$_3$ with TMS): ppm 69.9, 65.8, 52.5, 50.0, 31.8, 30.1, 29.5, 29.2, 27.2, 22.5, 13.9 m/z (DCl/MS): 260 [M+H]$^+$

Synthesis of N-(2,3-dihydroxypropyl)-N-tetradecylamine

Tetradecylamine (28.80 g, 0.13 mole) was heated to 85° C. Glycidol (10.00 g, 0.13 mole) was added dropwise. The reaction solution was heated under nitrogen for 3 hours and then was stirred overnight at room temperature. A white solid was obtained (crude yield=38.45 g). The solid was recrystalized from hot hexane (yield=12.2 g).

m.p.: 75°–79° C.

IR (nujol film, $cm^{-1}$): 3340 st, 3290 m, 3000–2840 br, 1460 st, 1380 m $^1$H NMR (200 MHz, warm CDCl$_3$ with TMS): δ 0.9 (br t, 3H), 1.2 (br s, 22H), 1.45 (m, 2H), 2.7 (m, 7H), 3.7 (m, 3H)

$^{13}$C NMR (50 MHz, warm CDCl$_3$ with TMS): ppm 69.7, 65.8, 52.5, 50.0, 31.8, 30.1, 29.6, 29.2, 27.2, 22.6, 13.9 m/z (DCl/MS): 288 [M+H]$^+$

Synthesis of N-(2,3-dihydroxypropyl)-N-hexadecylamine

Hexadecylamine (767 g, 3.17 mole) was dissolved in absolute ethanol. Glycidol (112 g, 1.58 mole) was added to the amine dropwise. The reaction was refluxed under nitrogen for 16 hours and then stirred at room temperature overnight. A white solid was obtained and filtered. The solid was washed with ether, filtered and recrystallized from hot ethanol. (yield 245 g).

Alternative Synthesis of N-(2,3-dihydroxypropyl)-N-hexadecylamine 3-chloro-1,2-propanediol reaction:

Hexadecylamine (12.3 g, 0.11 mole) and potassium carbonate (20.0 g, 0.15 mole) were dissolved in ethanol and refluxed. 3-chloro-1,2-propanediol (26.9 g, 0.11 mole) was added dropwise to the reaction with stirring. The reaction proceeded for several hours. The salts obtained were filtered and the ethanol was concentrated. The sample was recrystalized from hot hexane. (Yield=22.0 g).

Analysis of N-(2,3-dihydroxypropyl)-N-hexadecylamine was as follows:

m.p.=78.7°–80.7° C.

IR (nujol film, cm$^{-1}$): 3320 w, 2920 st, 2860 st, 1460 st, 1385 st $^1$H NMR (200 MHz, warm CDCl$_3$ with TMS): δ 0.85 (t, 3H), 1.3 (br s, 25H), 1.5 (m, 2H), 2.7 (m, 8H), 3.7 (m, 3H)

$^{13}$C NMR (50 MHz, warm CDCl$_3$ with TMS): ppm 69.8, 65.8, 52.5, 50.1, 31.8, 30.1, 29.6, 29.2, 27.2, 22.6, 13.9 m/z (DCl/MS): 316.2 [M+H]$^+$

Synthesis of N-(2,3-dihydroxypropyl)-N-octadecylamine

Octadecylamine (9.09 g, 0.034 mole) was dissolved in absolute ethanol. Glycidol (5.00 g, 0.068 mole) was added to the amine dropwise. The reaction solution was refluxed under nitrogen for 4 hours and then was stirred overnight at room temperature. A white solid was obtained (crude yield= 10.8 g). The solid was recrystalized from hot hexane. (Yield=6.9 g).

m.p.: 89°–91° C.

IR (nujol film, cm$^{-1}$): 3340 m, 3290 w, 2940 st, 2860 st, 1475 m, 1385 m $^1$H NMR (200MHz, warm CDCl$_3$ with TMS): δ 0.85 (br t, 3H), 1.25 (br s, 30 H), 1.45 (br s, 2H), 2.45 (m, 8H), 3.65 (m, 2H)

$^{13}$C NMR (50 MHz, warm CDCl$_3$ with TMS): ppm 69.83, 65.73, 52.43, 49.95, 31.74, 30.04, 29.49, 29.13, 27.13, 22.43, 13.68 m/z (DCl/MS): 344 [M+H]$^+$

Table 1 summarizes the characteristics of some neosphingosines that were synthesized:

TABLE 1

Results of Neosphingosine syntheses

| Starting Alkylamine | Neospingosine m.p. | Crude Neosphingosine Yield |
|---|---|---|
| Dodecylamine | 74–76 | 95% |
| Tetradecylamine | 73–75 | 99% |
| Hexadecylamine | 79–81 | 98% |
| Octyldecylamine | 89–91 | 93% |
| Oleylamine | — | quantitative |

Most of the reactions resulted in nearly quantitative yields (shown in Table 1). Neosphingosines were recrystallized from hot hexane for analytical purposes only. The recrystallization gave a moderate to low yield. It appeared that the product was partially soluble in the solvent. The concentration of solvent in vacuo resulted in the recovery of the product.

The neosphingosines were characterized by common analytical methods. IR showed both amine and hydroxy stretching frequency bands at 3340 and 3100 cm−1. MS spectrometry also supported our structural interpretation.

Synthesis of N-(2,3-dihydroxypropyl)-N-dodecyl Hexadecanamide (Structure 1)

N-(2,3-dihydroxypropyl)-N-dodecylamine (0.50 g, 0.0019 mole) and potassium hydroxide (0.01 g, 0.18 mmole) were heated to 85° C. under vacuum. Methyl palmitate (0.57 g, 0.0021 mole) was heated and added dropwise to the reaction. The reaction was heated under vacuum for 6 hours. A waxy off-white solid was obtained (crude yield=0.92 g) The waxy solid was recrystalized from hot hexane (yield= 0.6 g).

m.p.: 35°–38° C.

IR (nujol film, cm$^{-1}$): 3340 br st, 2960 st, 2860 st, 1630 st, 1460 st $^1$H NMR (200 MHz, CDCl$_3$ with TMS): δ 0.9 (br t, 6H), 1.3 (br s, 44H), 1.6 (br s, 4H), 2.3 (t, 2H), 3.2–3.7 (br m, 7H)

$^{13}$C NMR (50 MHz, CDCl$_3$ with TMS): ppm 175.4, 71.1, 63.8, 49.8, 49.3, 33.0, 31.8, 29.6, 29.4, 29.3, 29.0, 26.8, 25.4, 22.6, 13.9 m/z (DCl/MS): 498 [M+H]$^+$

Synthesis of N-(2,3-dihydroxypropyl)-N-tetradecylhexadecanamide (Structure 8)

N-(2,3-dihydroxypropyl)-N-tetradecylamine (1.0 g, 0.0035 moles) and potassium hydroxide (0.01 g, 0.18 mmole) were heated to 85° C. under vacuum. Methyl palmitate (1.036 g, 0.0038 mole) was heated to melt and added dropwise to the reaction. The reaction was heated under vacuum for 6 hours. A waxy off-white solid was obtained (crude yield=1.77 g). The waxy solid was recrystalized from hot hexane (yield=0.33 g).

m.p.: 55°–56° C.

IR (nujol film, cm$^{-1}$): 3440 br st, 2920 vs, 2860 vs, 1620 st, 1470 st, 1380 st $^1$H NMR (200 MHz, CDCl$_3$ with TMS): δ 0.95 (br t, 6H), 1.35 (br s, 50H), 1.6 (br m, 2H), 2.4 (t, 2H), 3.5 (m, 7H)

$^{13}$C NMR (50 MHz, CDCl$_3$ with TMS): ppm 169.10, 70.36, 66.18, 51.17, 50.24, 34.76, 34.24, 33.21, 31.96, 31.60, 29.70, 29.36, 29.11, 26.92, 25.46, 25.35, 25.05, 22.64, 14.10, 13.95 m/z (DCl/MS): 526.6 [M+H]$^+$

Synthesis of N-(2,3-dihydroxypropyl)-N-hexadecylhexadecanamide (Structure 4)

N-(2,3-dihydroxypropyl)-N-hexadecylamine (0.40 g, 0.0013 mole) and potassium hydroxide (0.01 g, 0.18 mmole) were heated to 85° C. under vacuum. Methyl palmitate (0.343 g, 0.0013 mole) was heated to melt and added dropwise to the reaction. The reaction was heated under vacuum for 6 hours. A waxy off-white solid was obtained. The waxy solid was recrystalized from hot hexane (yield= 0.4 g).

m.p.: 54°–57° C.

IR (nujol film, cm$^{-1}$): 3320 br, 3210 br, 2910 st, 2840 st, 1610 st, 1460 m $^1$H NMR (200MHz, CDCl$_3$ with TMS): δ 0.9 (br t, 6H), 1.3 (br s, 52H), 1,65 (m, 2 H), 2.35 (t, 2H), 3.2 (m, 2H), 3.7 (m, 7H)

$^{13}$C NMR (50 MHz, CDCl$_3$ with TMS): ppm 175.5, 70.8, 63.5, 49.7, 48.9, 32.9, 31.8, 29.6, 29.49, 29.40, 29.3, 28.9, 26.7, 25.4, 22.6, 14.1 m/z (DCl/MS): 554 [M+H]$^+$

Synthesis of
N-(2,3-dihydroxypropyl)-N-octadecylhexadecanamide
(Structure 10)

N-(2,3-dihydroxypropyl)-octadecylamine (1.0 g, 0.0029 mole) and potassium hydroxide (0.01 g, 0.18 mmole) were heated to 85° C. under vacuum. Methyl palmitate (0.7885 g, 0.0029 mole) was heated and added dropwise to the reaction. The reaction was heated under vacuum for 6 hours. A waxy off-white solid was obtained (crude yield=1.59 g). The waxy solid was recrystalized from hot hexane (yield=0.99 g).

m.p.: 54°–56° C.

IR (Nujol film, cm$^{-1}$): 3380 m, 3290 m, 2940 vs, 2860 vs, 1610 st, 1480 st, 1385 st $^1$H NMR (200 MHz, CDCl$_3$ with TMS): δ 0.9 (br t, 6H), 1.25 (br s, 56), 1.7 (br m, 4H), 2.3 (br s, 2H), 3.6 (br m, 7H)

$^{13}$C NMR (50 MHz, CDCl$_3$ with TMS): ppm 175.42, 70.86, 63.65, 49.81, 48.92, 33.06, 31.96, 29.71, 28.97, 26.83, 25.52, 22.73, 14.14

Synthesis of N-(2,3-dihydroxypropyl)-N-dodecyl-2-hydroxyoctanamide (Structure 2)

N-(2,3-dihydroxypropyl)-N-dodecylamine (1.0 g, 0.0039 mole) and potassium hydroxide (0.01 g, 0.18 mmole) were heated to 85° C. under vacuum and methyl 2-hydroxyoctanoate (0.6718 g, 0.0039 mole) was added dropwise to the reaction. The reaction was heated under vacuum for 5 hours. A waxy off-white solid was obtained (crude yield=1.38 g). The waxy solid was recrystalized from hot hexane (yield= 0.44 g).

m.p.: 68°–71° C.

IR (nujol film, cm$^{-1}$): 3410 w, 3340 w, 2920 st, 2860 st, 1610 m, 1460 m $^1$H NMR (200 MHz, CDCl$_3$ with TMS): δ 0.80 (br s, 6H), 1.3 (br s, 28H), 2.6 (m, 2H), 3.5 (m, 10H), 4.3 (m, 1H)

$^{13}$C NMR (50 MHz, CDCl$_3$ with TMS): ppm 176.12, 70.45, 68.21, 63.69, 49.89, 48.80, 35.38, 31.84, 31.66, 29.58, 29.49, 29.29, 28.97, 28.85, 27.23, 26.70, 25.12, 22.61, 22.53, 14.04 m/z (DCl/MS): 402,3 [M+H]$^+$

Synthesis of
N-(2,3-dihydroxypropyl)-N-tetradecyl-2-hydroxyoctanamide (Structure 7)

N-(2,3-dihydroxypropyl)-N-tetradecylamine (1.0 g, 0.0035 mole) and potassium hydroxide (0.01 g, 0.18 mmole) were heated to 85° C. under vacuum and methyl-2-hydroxyoctanoate (0.667 g, 0.0038 mole) was added dropwise to the reaction. The reaction was heated under vacuum for 5 hours. A waxy off-white solid was obtained (crude yield=1.33 g). The waxy solid was recrystalized from hot hexane (yield= 0.4 g).

m.p.: 69°–72° C.

IR (nujol film, cm$^{-1}$): 3420 st, 3220 st, 2950 vs, 2860 vs, 1610 st $^1$H NMR (200 MHz, CDCl$_3$ with TMS): 8 0.9 (br s, 3H), 1.3 (br s, 33H), 1.5 (m, 2H), 3.3–3.9 (m, 11H), 4.25 (m, 1H)

$^{13}$C NMR (50 MHz, CDCl$_3$ with TMS): ppm 176.2, 70.52, 68.23, 63.67, 48.77, 35.42, 31.85, 31.67, 29.60, 29.29, 28.96, 28.85, 27.24, 26.89, 26.70, 25.09, 24.86, 22.62, 22.54, 14.01 m/z (DCl/MS): 430 [M+H]$^+$

Synthesis of
N-(2,3-dihydroxypropyl)-N-hexadecyl-2-hydroxyoctanamide (Structure 5)

N-(2,3-dihydroxypropyl)-N-hexadecylamine (1.0 g, 0.0032 mole) and potassium hydroxide (0.01 g, 0.18 mmole) were heated to 85° C. under vacuum and methyl-2-hydroxyoctanoate (0.55 g, 0.0032 mole) was heated and added dropwise to the reaction. The reaction was heated under vacuum for 6 hours. A waxy off-white solid was obtained (crude yield=1.39 g). The waxy solid was recrystalized from hot hexane (yield=0.88 g).

m.p.: 67°–70° C.

IR (Nujol film, cm$^{-1}$): 3410 st, 3360 st, 2940 vs, 2880 vs, 1615 st, 1480 st, 1390 m $^1$H NMR (200 MHz, CDCl$_3$ with TMS): δ 0.88 (br t, 6H), 1.25 (br s, 36H), 1.55 (br m, 2H), 2.6–4.3 (br m, 9H)

$^{13}$C NMR (50 MHz, CDCl$_3$ with TMS): ppm 176.36, 70.62, 68.25, 62.61, 49.93, 48.79, 35.50, 31.89, 31.68, 30.06, 29.88, 29.66, 29.33, 28.99, 27.25, 22.66, 22.56, 14.08

Synthesis of N
-(2,3-dihydroxypropyl)-N-dodecyl-2-hydroxyhexadecanamide (Structure 3)

N-(2,3-dihydroxypropyl)-N-dodecylamine (1.00 g, 0.0039 mole) and potassium hydroxide (0.01 g, 0.18 mmole) were heated to 85° C. under vacuum and methyl-2-hydroxyhexadecanoate (1.12 g, 0.0039 mole) was heated and added dropwise to the reaction. The reaction was heated under vacuum for 6 hours. A waxy off-white solid was obtained (crude yield=1.9 g). The waxy solid was recrystalized from hot hexane (yield=1.26 g).

m.p.: 56°–59° C.

IR (Nujol film, cm$^{-1}$): 3360 br st, 2940 st, 2880 st, 1620 st, 1480 st $^1$H NMR (200 MHz, CDCl$_3$ with TMS): δ 0.9 (br t, 6H), 1.25 (br s, 46H), 1.45 (br m, 2H), 2.8 (br m, 2H), 3.6 (br m, 7H)

$^{13}$C NMR (50 MHz, CDCl$_3$ with TMS): ppm 175.9, 70.2, 67.9, 65.5, 49.9, 35.3, 31.6, 31.5, 29.5, 28.9, 28.8, 27.3, 26.9, 26.5, 25.0, 24.5, 15.1

Synthesis of
N-(2,3-dihydroxypropyl)-N-tetradecyl-2-hydroxyhexadecanamide. (Structure 9)

N-(2,3-dihydroxypropyl)-N-tetradecylamine (1.00 g, 0.0035 mole) and potassium hydroxide (0.01 g, 0.18 mmole) were heated to 85° C. under vacuum and methyl 2-hydroxyhexadecanoate (0.94 g, 0.0035 mole) was heated and added dropwise to the reaction. The reaction was heated under vacuum for 6 hours. A waxy off-white solid was obtained (crude yield=1.8 g). The waxy solid was recrystalized from hot hexane (yield=1.09 g)

m.p.: 67°–70° C.

IR (Nujol film, cm$^{-1}$): 3410 br m, 3330 br m, 2950 vs, 2860 vs, 1605 st, 1470 st $^1$H NMR (200 MHz, CDCl$_3$ with TMS): δ 0.9 (br t, 6H), 1.3 (br s, 50H), 1.55 (br m, 2H), 2.8 (m, 2H), 3.65 (m, 7H)

$^{13}$C NMR (50 MHz, CDCl$_3$ with TMS): ppm 176.77, 72.53, 68.43, 64.0, 49.23, 48.9, 35.13, 31.92, 29.67, 29.32, 26.93, 25.26, 22.63, 13.94

Synthesis of
N-(2,3-dihydroxypropyl)-N-hexadecyl-2-hydroxyhexadecanamide (Structure 6)

N-(2,3-dihydroxypropyl)-N-hexadecylamine (1.0 g, 0.0032 mole) and potassium hydroxide (0.01 g, 0.18 mmole) were heated to 85° C. under vacuum and methyl 2-hydroxyhexadecanoate (0.907 g, 0.0032 mole) was heated and added dropwise to the reaction. The reaction was heated under vacuum for 6 hours. A waxy off-white solid was obtained (crude yield=1.79 g). The waxy solid was recrystalized from hot hexane (yield=0.94 g).

m.p.: 62°–64° C.

IR (Nujol film, cm$^{-1}$): 3360 br m, 2910 vs, 2860 vs, 1610 st, 1470 st $^1$H NMR (200 MHz, CDCl$_3$ with TMS): δ 0.89 (br t, 6H), 1.28 (br s, 54H), 1.65 (m, 2H), 2.65 (m, 2H), 3.9 (br m, 7H)

$^{13}$C NMR (50 MHz, CDCl$_3$ with TMS)

Neoceramides were characterized-by common analytical methods. IR showed hydroxy stretching frequency bands at 3340–3100 cm$^{-1}$, and amide stretching frequencies at 1680 cm$^{-1}$. Amide carbon was observed approximately 175 ppm in carbon-13 experiments. Neoceramides were recrystallized from hot hexane for analytical characterization only.

Table 2 summarizes the characteristics of some of the neoceramides that were synthesized.

TABLE 2

Results of Neoceramide Syntheses

| Structure | m.p. | Crude Neoceramide Yield |
|---|---|---|
| 1 | 35–37 | 96% |
| 4 | 56–57 | 94% |
| 2 | 68–71 | 89% |
| 7 | 68–70 | 89% |
| 3 | 56–59 | 90% |
| 6 | 62–64 | 92% |
| 8 | 55–56 | 96% |
| 10 | 54–56 | 93% |
| 5 | 67–70 | 94% |
| 9 | 67–70 | 95% |

EXAMPLE 2

In vitro Measurement of Water Vapour Transmission Rate (WVTR)

The reduction in water permeability of the skin following topical application of the neoceramide according to the present invention can be determined by in vitro measurement of the water vapour transmission rate (WVTR) using a water transmission cell adapted from that described by Blank I. H., J. Invest. Dermatol., (1952), 18, 433–440.

Pretreatment of Porcine Stratum Corneum

Isolated porcine stratum corneum was floated on 2-propanol contained in a glass petri dish. The dish was gently agitated for 1 hour at 40° C. and the sample of extracted stratum corneum was then removed, floated in saline solution onto spectra mesh and air dried overnight.

Measurement of Initial WVTR Prior to Treatment

750 μl distilled water was placed in the center well of the cell and a sample of pretreated stratum corneum (see above) was carefully laid onto a stainless steel grid over the well ensuring that the stratum corneum completely covered the O-ring, such that a watertight seal was achieved. Care was taken to avoid wrinkles, tears and holes in the stratum corneum sample. The transmission cell was then screwed into position and allowed to equilibrate at room temperature before an initial measurement was made. The cell was weighed after 30 minutes, then placed in an incubator at 37° C., 5% relative humidity. Two further weight measurements were taken at suitable intervals over a period of 24 hours at the end of which time a test or control solution was applied and two more measurements were taken during a further 21 hours. Five cells were used for each test or control treatment.

Study of the Effect of Topical Application of Test Material

For each test, a solution of test material in chloroform/methanol (2:1 v/v) was prepared at 15 mg/mL concentration 15 μl of this solution was applied to the previously selected 2-propanol extracted skin samples as described above. The chloroform/methanol quickly evaporated. The five cells containing the skin samples were weighed after 5 minutes prior to placing in the incubator at 37° C., 0% RH. As mentioned above, two weight measurements were then taken at intervals over a period of 21 hours.

A negative control was conducted by adding an equal quantity of the solvent without any test material. A positive control was conducted by adding an equal quantity of the solvent containing skin lipid as the test material; the skin lipid was collected from the partial delipidization of the corneum by isopropanol, followed by removal of the solvent and the lipid obtained was dissolved in chloroform/methanol (2:1 v/v) at 15 mg/ml.

Calculation of the WVTR

The WVTR was calculated for each sample (pre and post topical application) as follows:

$$WVTR(mg/cm^2/hr) = \frac{weight\ loss}{Area\ of\ exposed\ tissue \times time}$$

The mean WVTR for each group of cells was then calculated from these values. The standard deviation was calculated from the observed changes (relative increase or decrease) in WVTR measured before and after the topical application.

Neoceramide WVTR Results

WVTR results are reported as % reduction which is a ratio of the reduction in water vapor transmission (in mg/cm$^2$/hr) achieved by the test material compared with the same piece of stratum corneum before treatment. The skin lipid is not a single lipid, but a complex lipid mixture. Pseudoceramide X is a pseudoceramide according to U.S. Pat. Nos. 4,778,823 (Kawamato et al.), or 4,985,547 (Yano et al.), or 5,175,321 (Qhashi et al.) Pseudoceramide Y is a pseudoceramide according to U.S. Pat. No. 5,198,210 (Critchley et al.). Pseudoceramides X and Y are represented by the following structures:

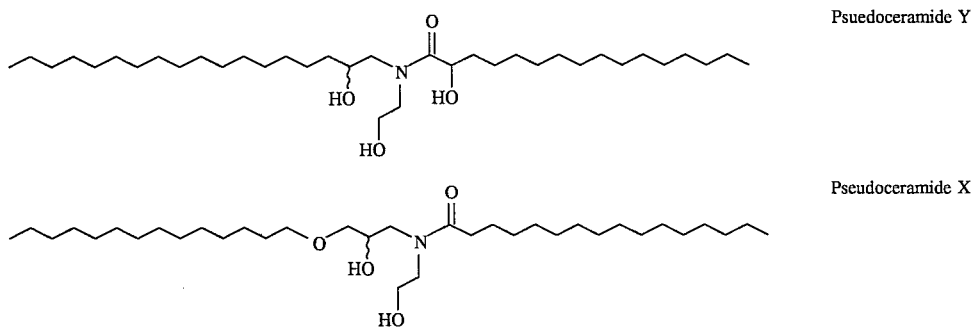

Psuedoceramide Y

Pseudoceramide X

The results that were obtained are summarized in Table 3.

TABLE 3

| TEST MATERIAL | CONC/CELI (μg) | WVTR In % Reduction |
|---|---|---|
| Negative Control | — | −5 ± 11 |
| Skin Lipid | 286 | 49 ± 15 |
| Pseudoceramide X | 306 | 35.2 ± 10 |
| Pseudoceramide Y | 306 | 46 ± 12 |
| Neoceramide of Structure 2 | 143 | 38.2 ± 10 |
| Neoceramide of Structure 4 | 286 | 39.9 ± 13 |
| Neoceramide of Structure 1 | 143 | 33.4 ± 10 |
| Neoceramide of Structure 7 | 286 | 35.1 ± 11 |

The results demonstrate that neoceramides within the scope of the present inventive performed as well as prior art pseudoceramides X and Y. The inventive neoceramides also performed well when compared with natural skin lipid.

EXAMPLE 3

DISPERSION TEST PROCEDURE

Test 1

0.1 g of a lipid was added to 1 mL water at 62° C. The resulting mixture was vortexed (Vortex-Genie from Scientific Industries Inc.), then mixed at Speed 7 for 10 sec. and sonicated until dispersed. Sonication performed with Branson 1200 Ultrasonic Bath (from Branson). The results that were obtained are summarized in Table 4.

TABLE 4

| LIPID | TEMPERATURE | SONICATION TIME | Observations |
|---|---|---|---|
| Pseudoceramide Y | 62° C. | 7 minutes | Very viscous gel |
| Pseudoceramide X | 62° C. | 50 minutes | Not dispersed |
| Neoceramide of Structure 4 | 62° C. | 11.5 minutes | Well dispersed liquid |
| Neoceramide of Structure 5 | 62° C. | 5.25 minutes | Well dispersed liquid |

Test 2

0.25 g of a lipid were added to 5 mLs water@50° C. The resulting admixture was subjected to sequential mixing sonication steps as follows: Vortex mix for 10 seconds, then sonicate 10 minutes, then vortex mix 15 seconds, then sonicate 10 minutes, then vortex mix for 20 seconds, then sonicate 10 minutes, then vortex mix for 10 seconds–15 seconds, then sonicate until the state indicated in the table resulted. The results that were obtained are summarized in Table 5.

TABLE 5

| LIPID | TEMPERATURE | TOTAL SONICATION TIME | TOTAL MIX TIME | OBSERVATION |
|---|---|---|---|---|
| Neoceramide of Structure 4 | 50° C. | 36 minutes | 60 sec. | Well dispersed liquid |
| Neoceramide of Structure 5 | 50° C. | 36 minutes | 55 sec. | Well dispersed liquid |
| Pseudoceramide Y | 50° C. | 36 minutes | 55 sec. | Very viscous gel |
| Pseudoceramide X | 50° C. | 50 minutes | 55 sec. | Remained solid, not dispersed |

The results in Tables 4 and 5 demonstrate that neoceramides within the scope of the invention dispersed well in water at both 50° C. and at 62° C. while previously known pseudoceramides either formed very viscous gels or did not disperse at all.

EXAMPLE 4

Preparation of Aqueous Lotions

The aqueous lotions all of which contain 4 wt % oil phase as indicated in Table 6 below were prepared:

TABLE 6

| INGREDIENT | TRADENAME AND SUPPLIER | WEIGHT % IN FORMULATION | | | | | | |
|---|---|---|---|---|---|---|---|---|
| | | a | b | c | d | e | f | g |
| OIL PHASE COMPONENTS | | | | | | | | |
| Neoceramide of Structure 4 | | 3 | 0 | 0 | 1 | 0 | 0 | 0 |
| Pseudoceramide X | | 0 | 3 | 0 | 0 | 1 | 0 | 0 |
| Sucrose distearate | Ryoto S270 ® (Mitsubishi Kasei) | 0 | 0 | 3 | 0 | 0 | 1 | 0 |
| Cholesterol | (Lancaster Synthesis) | 0 | 0 | 0 | 2 | 2 | 2 | 3 |
| Stearic acid | Pristerene 4911 ® (Unichema) | 0.7 | 0.7 | 0.7 | 0.7 | 0.7 | 0.7 | 0.7 |
| Sodium stearate | (Witco) | 0.3 | 0.3 | 0.3 | 0.3 | 0.3 | 0.3 | 0.3 |
| WATER PHASE COMPONENTS | | | | | | | | |
| Glycerin | (J. T. Baker) | 1 | 1 | 1 | 1 | 1 | 1 | 1 |
| Xanthan Gum | Keltrol 100 ® (Kelco Corp.) | 0.5 | 0.5 | 0.5 | 0.5 | 0.5 | 0.5 | 0.5 |
| DMDM Hydantoin and Iodopropynl butyl carbamate | Glydant Plus ® (Lonza) | 0.2 | 0.2 | 0.2 | 0.2 | 0.2 | 0.2 | 0.2 |
| Water | | 94.3 | 94.3 | 94.3 | 94.3 | 94.3 | 94.3 | 94.3 |

These lotions were prepared by first mixing the water phase components under high agitation (2000) rpm using a cage stirring rod and overhead mixer at 60° C. for 30 minutes. The oil phase components were separately melted together at 100° C.–150° C. and mixed thoroughly by hand using a spatula. The water phase was added to the oil phase with heavy mixing (2000 rpm). When all the water phase was added, the temperature was maintained at 80° C. with continued mixing for an additional 30 minutes. Then the contents were allowed to cool to room temperature while mixing continued. Finally the amount of water that was lost due to evaporation was replaced and the final lotion mixed at room temperature for 10 minutes.

Procedure to Determine In-vitro Water Barrier Efficiency of Aqueous Lotions

The effectiveness of the above lotions in forming "water barriers" to prevent water loss were examined as follows:

Known weights of the test lotions were spread evenly over a 25 mm, 5 micron Acetate Plus membrane (Micron separations Inc) and allowed to dry overnight. The amount of lotion taken for comparison was such that the residual dry weight of material in each case was 15 mg. The treated membranes were placed, treated side up, in diffusion cells containing 1.5 g of water; the diffusion cells were similar to those described in Example 2. The cells were placed in a dessicator containing anhydrous calcium sulfate and left undisturbed for 20 hours at room temperature after which the amount of water lost was determined by weighing.

In each test 12 cells were prepared; 4 membranes treated with one lotion, 4 with another lotion and 4 untreated membranes as controls. The results for each of the lotion treatments are reported as % reduction in water loss calculated as:

% reduction in water loss=$100 \times (w1-w2)/w1$ where w1 is the average weight loss in untreated cells and w2 is the average weight loss in the cells treated with a particular lotion. The standard deviations were obtained from the variability of the treated samples in each test.

Results

Binary (Cholesterol-free) Systems

The effectiveness of the inventive neoceramides in reducing water loss was compared to Pseudoceramide X or sucrose distearate in combination with fatty acid but in cholesterol free formulations. The results are summarized in Table 7. Sucrose distearate was referred to as an allegedly effective water barrier forming glycolipid in EP 556 957.

TABLE 7

| FORMULATION | % REDUCTION IN WATER LOSS |
|---|---|
| Example 4a in Table 6 (Neoceramide of Structure 4) | 62 ± 2 |
| Example 4b in Table 6 (Pseudoceramide X) | 23 ± 3 |
| Example 4c in Table 6 (sucrose distearate) | 31 ± 1 |

Ternary (Cholesterol Containing) Systems

Similar comparative water loss experiments were conducted with ternary active lotions containing either the inventive neoceramide of structure 4 (example 4d in Table 6) or previously known lipids-pseudoceramide X (example 4e in Table 6) or sucrose distearate (example 4f in Table 6) in combination with cholesterol and fatty acid. The control lotion containing only cholesterol and fatty acid (example 4 g in Table 6) was included for comparison. The results are shown in Table 8.

TABLE 8

| FORMULATION | % REDUCTION IN WATER LOSS |
|---|---|
| Example 4d in Table 6 (Neoceramide of Structure 4) | 50 ± 2 |
| Example 4e in Table 6 (Pseudoceramide X) | 32 ± 3 |
| Example 4f in Table 6 (sucrose distearate) | 42 ± 3 |
| Example 4g in Table 6 (cholesterol control) | 6 ± 2 |

The results from Tables 7 and 8 show that the inventive neoceramides offer significant improvement when used as barrier forming compositions compared to previously known lipids. Importantly, the results show that unlike the previously known lipids which require the presence of cholesterol for maximum benefits, the efficiency of the inventive neoceramide improves in cholesterol-free formulations.

The results from Tables 7 and 8 also show that the inventive cholesterol-free compositions perform better than the inventive compositions containing cholesterol.

EXAMPLE 5

The following lotions within the scope of the invention were prepared:

| INGREDIENT | EXAMPLE 5A | EXAMPLE 5B | EXAMPLE 5C | EXAMPLE 5D |
|---|---|---|---|---|
| Water | 68.125 | 68.125 | 69.920 | 69.920 |
| Disodium EDTA | 0.075 | 0.075 | 0.080 | 0.080 |
| Magnesium Aluminum Silicate | 0.750 | 0.750 | | |
| Sodium Chloride | | | 1.000 | 1.000 |
| Butylene Glycol | 3.000 | 3.000 | 3.000 | 3.000 |
| Methylparaben | 0.150 | 0.150 | 0.150 | 0.150 |
| Xanthan Gum | 0.400 | 0.400 | | |
| $C_{12-15}$ Alcohols Benzoate | 20.000 | 20.000 | 22.000 | 22.000 |
| Neoceramide of Structure 4 | 1.000 | | 1.000 | |
| Neoceramide of Structure 5 | | 1.000 | | 1.000 |
| Propylparaben | 0.100 | 0.100 | 0.100 | 0.100 |
| Stearic Acid | 0.500 | 0.500 | 0.200 | 0.200 |
| Cetyl Alcohol | 0.250 | 0.250 | 0.200 | 0.200 |
| Phenoxyethanol | 0.350 | 0.350 | 0.350 | 0.350 |
| Triethanolamine 99% | 0.500 | 0.500 | | |
| Steareth-21 | 2.000 | 2.000 | | |
| Steareth-2 | 2.800 | 2.800 | | |
| Cetyl Dimethicone Copolyol | | | 2.000 | 2.000 |
| TOTALS: | 100.000 | 100.000 | 100.000 | 100.000 |
| Emulsion Type | oil-in-water | oil-in-water | water-in-oil | water-in-oil |

EXAMPLE 6

This example illustrates a high internal phase water-in-oil emulsion in accordance with the invention.

| | % w/w |
|---|---|
| Fully hydrogenated coconut oil | 3.9 |
| Neoceramide having the structure (5) | 0.1 |
| Oleth-2 | 5 |

-continued

|  | % w/w |
|---|---|
| Quaternium-18-Hectorite | 0.5 |
| Preservative | 0.3 |
| $MgSO_4 7H_2O$ | 0.3 |
| Butylated hydroxy toluene | 0.01 |
| Perfume | qs |
| Water | to 100 |

EXAMPLE 7

This example also illustrates a high internal phase water-in-oil emulsion in accordance with the invention in which the formulation of Example 6 is prepared but with the following changes:

(i) liquid paraffin is used in place of the fully hydrogenated coconut oil, and (ii) the neoceramide of structure (6) is used.

EXAMPLE 8

This example also illustrates a high internal phase water-in-oil emulsion in accordance with the invention in which the formulation of Example 6 is prepared but with the following changes:

The neoceramide of structure (7) is used.

EXAMPLE 9

This example illustrates an oil-in-water cream in accordance with the invention.

|  | % w/w |
|---|---|
| Mineral oil | 4 |
| Neoceramide having the structure (8) | 0.1 |
| Ceteth-10 | 4 |
| Cetyl Alcohol | 4 |
| Triethanolamine | 0.75 |
| Butane-1,3-diol | 3 |
| Xanthan Gum | 0.3 |
| Preservative | 0.4 |
| Perfume | qs |
| Butylated hydroxy toluene | 0.01 |
| Water | to 100 |

EXAMPLES 10 and 11

The following compositions according to the invention represent lotions which can be used in the treatment of dry skin:

|  | % w/w | |
|---|---|---|
|  | 10 | 11 |
| Neoceramide having the structure (2) | 1.5 | — |
| Neoceramide having the structure (3) | — | 0.1 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Water | to 100 | to 100 |

EXAMPLE 12

This example illustrates a high internal phase water-in-oil emulsion in accordance with the invention.

|  | % w/w |
|---|---|
| Fully hydrogenated coconut oil | 3.9 |
| Neoceramide having the structure (1) | 0.1 |
| Oleth-2 | 5 |
| Quaternium-18-Hectorite | 0.5 |
| Preservative | 0.3 |
| $MgSO_4 7H_2O$ | 0.3 |
| Butylated hydroxy toluene | 0.010 |
| Perfume | qs |
| Water | to 100 |

EXAMPLE 13

This example illustrates an alcoholic lotion containing an inventive neoceramide which is suitable for application to nails.

|  | % w/w |
|---|---|
| Neoceramide having the structure (9) | 0.2 |
| Dimethylsulphoxide | 10 |
| Ethanol | 40 |
| Antoxidant | 0.1 |
| Perfume | qs |
| Water | to 100 |

EXAMPLES 14 and 15

The following compositions according to the invention represent lotions which can be used in the treatment of dry, unmanageable hair.

|  | % w/w | |
|---|---|---|
|  | 14 | 15 |
| Neoceramide having the structure (9) | 1.5 | — |
| Neoceramide having the structure (10) | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilized demineralized water | to 100 | to 100 |

It should be understood that the specific forms of the invention herein illustrated and described are intended to be representative only. Changes, including but not limited to those suggested in this specification, may be made in the illustrated embodiments without departing from the clear teaching of the disclosure. Accordingly, reference should be made to the following appended claims in determining the full scope of the invention.

What is claimed is:

1. A composition for topical application to human skin, hair or nails, the composition comprising:

a) an effective amount of at least one neoceramide of Formula 1

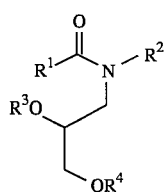

wherein

R¹ is a linear or branched, saturated or unsaturated, or hydroxylated aliphatic hydrocarbon group having from 7 to 48 carbon atoms;

R² is a linear or branched, saturated or unsaturated aliphatic hydrocarbon group having from 7 to 48 carbon atoms;

R³ and R⁴ are the same or different and each is selected from the group consisting of phosphorylethyl amine, phosphorylethyl ammonium chloride, phosphorylethyl ammonium bromide and phosphorylethyl ammonium sulfate; and b) a cosmetically acceptable vehicle for the neoceramide.

2. The composition of claim 1 wherein the amount of the neoceramide is from 0.0001 to 20% by weight of the composition.

3. The composition of claim 1 further comprising an ingredient selected from the group consisting of a fatty acid, a fatty alcohol, and mixtures thereof.

4. The composition of claim 1 which is essentially free of a cholesterol or a plant sterol.

5. A method of treating skin, hair, or nails which comprises applying topically thereto the composition of claim 1.

6. A method of treating skin, hair, or nails which comprises applying topically thereto the composition of claim 4.

7. A neoceramide of Formula I:

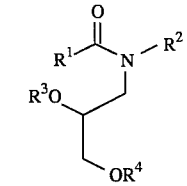

wherein

R¹ is a linear or branched, saturated or unsaturated, or hydroxylated aliphatic hydrocarbon group having from 7 to 48 carbon atoms;

R² is a linear or branched, saturated or unsaturated, aliphatic hydrocarbon group having from 7 to 48 carbon atoms;

R³ and R⁴ each is selected from the group consisting of phosphorylethyl amine, phosphorylethyl ammonium chloride, phosphorylethyl ammonium bromide and phosphorylethyl ammonium sulfate.

8. The neoceramide of claim 1 wherein the combined total number of carbon atoms in R¹ and R² is at least 18.

9. A method of treating skin, hair, or nails which comprises applying topically thereto an effective amount of the neoceramide of claim 1.

\* \* \* \* \*